Figure 1:
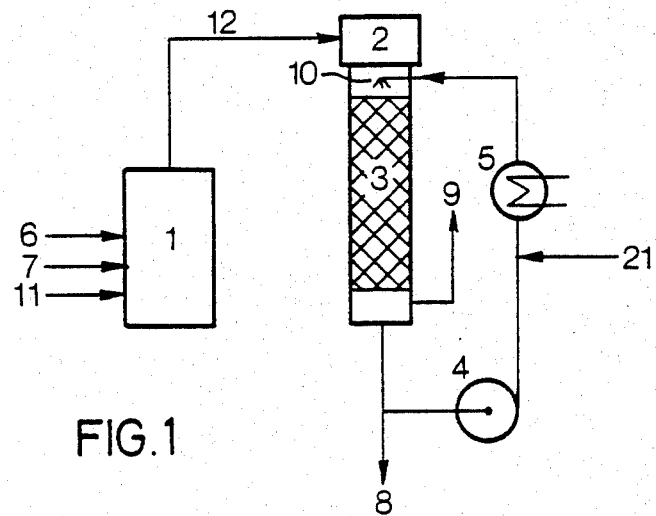

United States Patent [19]

Sauer et al.

[11] Patent Number: 4,511,739
[45] Date of Patent: Apr. 16, 1985

[54] CONTINUOUS PREPARATION OF GLYOXAL

[75] Inventors: Wolfgang Sauer, Mannheim; Wolfgang Hoffmann, Frankenthal, both of Fed. Rep. of Germany

[73] Assignee: BASF Aktiengesellschaft, Fed. Rep. of Germany

[21] Appl. No.: 153,704

[22] Filed: May 27, 1980

[30] Foreign Application Priority Data

Jun. 2, 1979 [DE] Fed. Rep. of Germany ....... 2922599

[51] Int. Cl.³ .......................................... C07C 47/127
[52] U.S. Cl. ..................................... 568/473; 568/471
[58] Field of Search ................................. 568/471, 473

[56] References Cited

U.S. PATENT DOCUMENTS 3,948,997  4/1976  Hoew et al. ........................ 568/473

FOREIGN PATENT DOCUMENTS

| 1032732 | 6/1958 | Fed. Rep. of Germany . |
| 1923048i | 5/1969 | Fed. Rep. of Germany . |
| 2634439 | 2/1977 | Fed. Rep. of Germany . |
| 836828 | 6/1960 | United Kingdom . |
| 1234766 | 6/1971 | United Kingdom ................ 568/471 |
| 1272592 | 5/1972 | United Kingdom ................ 568/471 |
| 1542900 | 3/1979 | United Kingdom . |
| 164262 | 8/1964 | U.S.S.R. ............................. 568/471 |

OTHER PUBLICATIONS

Bohmfalf et al., "Ind. and Eng. Chem.", vol. 43, (1951), pp. 786–794.
Foerst, "Ullmanns Encyklopadie der Technischen Chemie", vol. 8, pp. 250–252, (1957).

*Primary Examiner*—Werren B. Lone
*Attorney, Agent, or Firm*—Keil & Weinkauf

[57] ABSTRACT

Glyoxal is prepared by oxidizing glycol in the presence of a silver catalyst, with subsequent or partial condensation of glycol, glyoxal, glycol aldehyde, formaldehyde and/or water by treatment with water or aqueous glyoxal solution in fine dispersion, under specific conditions with regard to the temperature and dispersion of the treatment liquid.

The glyoxal which can be prepared by the process of the invention is a wrinkle-resist agent, an assistant for increasing the tear strength and elasticity of fiber materials, a tanning agent, a photographic hardener and a valuable starting material for the production of synthetic resins, textile assistants, paper assistants and plastics.

17 Claims, 3 Drawing Figures

CONTINUOUS PREPARATION OF GLYOXAL

The present invention relates to a process for the preparation of glyoxal by oxidizing glycol in the presence of a silver catalyst, with subsequent or partial condensation of glycol, glyoxal, glycol aldehyde, formaldehyde and/or water by treatment with water or aqueous glyoxal solution in fine dispersion, under specific conditions with regard to the temperature and dispersion of the treatment liquid.

Ullmans Encyklopädie der technischen Chemie, Volume 8, pages 250–252, discloses that one of the most important processes for the preparation of glyoxal is the oxidation of ethylene glycol with air. This process is carried out at from 573 to 598 K., using copper oxide as the catalyst and halogen compounds being added. A 32 percent strength glyoxal solution is obtained from the reaction mixture by absorption in a glyoxal solution or in water. Such a process gives yields of at most 65 percent and space-time yields of only from 0.04 to 1.5 grams of glyoxal per $cm^3$ of catalyst per hour. The condensation of fractions of product by spraying water into the hot reaction gases is not described. Since the glyoxal solution contains numerous by-products, which in the main are of strongly acidic character (loc. cit., page 251), the glyoxal must be separated from the solution by repeated fractional and azeotropic distillation.

The use of silver as the catalyst on pumice and aluminum as the carrier is disclosed in Proceed. Acad. Sci. USSR, Che. Ser. (1964), pages 641–643. The best result has been achieved using silver spirals, at 783 K. and under a pressure of from 544 to 816 mbar, the yield achieved being 69 percent. The product is obtained in the form of a 25 percent strength by weight aqueous solution which additionally contains from 5 to 10 percent of glycol; no further details are given with regard to the working up of the hot reaction gases.

Russian Patent 136,352 describes the oxidation of glycol at from 773 to 973 K. using silver-on-aluminum oxide (40% of Ag) as the catalyst. The yield is 61 percent and the space-time yield is 12.8 grams of glyoxal per hour per gram of catalyst. The process has the disadvantage that the preparation of the catalyst is involved and that a fairly dilute glycol solution has to be used. The separation of the product from the reaction gases is not described in more detail.

German Published Application DAS No. 1,032,732 states that a promoter, eg. $TiO_2$ or $Mo_2O_5$, is required when copper or silver is used as the catalyst and that inhibitors, eg. HCl, $Cl_2$ or ethylene dichloride, must be added in order to increase the yield. The best result obtained using this procedure is a space-time yield of 0.043 gram per $cm^3$ per hour. According to the above DAS, the result can be improved by applying the silver to pumice, silica gel or aluminum oxide as the carrier. The process is carried out at from 573 to 723 K., using an air/nitrogen mixture containing from 1.6 to 5 percent of oxygen. A space-time yield of 0.104 gram of glyoxal per $cm^3$ of catalyst per hour is obtained, the yield being 55 percent. Only Example 1 describes the procedure for working up the hot reaction gases. The starting mixture in the reactor is fed upward through the catalyst and the reaction gases are then fed into two successive wash towers, which are packed with Raschig rings and through which water is circulated by pumping.

German Laid-Open Application DOS No. 1,923,048 describes the preparation of glyoxal using a catalyst which consists of 2 components (a and b), (a) being copper or silver and/or gold and (b) being germanium, tin, lead, nitrogen, phosphorus, arsenic, antimony and/or bismuth.

Silver is preferably used in combination with tin, phosphorus and/or arsenic, and overall, in particular, copper is preferred to silver. The reaction temperature stated is from about 450 to 880 K., preferably from about 570 to 720 K. In comparison with the numerous Examples in which copper catalysts are used, only a single Example is given in which a copper-free silver catalyst (silver/phosphorus) is used and in this Example the reaction is carried out at from about 700 to 720 K. The space-time yield calculated from the data given is unsatisfactory. A further disadvantage is that the preparation of the catalyst is involved. In one embodiment, the reaction gases are cooled by means of a cooling zone (Example 6) to below the condensation point of ethylene glycol and above the condensation point of glyoxal, and ethylene glycol is thus separated from glyoxal, 2,3-dihydroxydioxane being formed as a by-product. Various purification steps are then carried out. Cooling by means of a cooling zone is apparently also described in further embodiments. Likewise, Example 1 shows that the product is condensed out of the hot reaction gases by cooling in two cooling zones and not by mixing with water. In Example 5, the hot gases are passed into a quenching solution, which is a crude glyoxal solution. This solution is then fed through a stripping column for formaldehyde (105° C.), an ion exchange column and a thin-film evaporator. Only for the purposes of heating and splitting the by-product 2,3-dihydroxydioxane (Example 6) is a solution of this substance in ethylene glycol allowed to impinge in the form of fine droplets onto a stream of gas, eg. nitrogen, at a high temperature and a high flow rate. The formaldehyde can be separated off by flushing out the aqueous glyoxal solution with a mixture of steam and nitrogen at elevated temperature. Organic acids and colored impurities in the reaction gases must be separated off from the aqueous glyoxal solution by means of weakly basic anion exchangers after the formaldehyde has been separated off, very dilute glyoxal solutions being preferably used for this step. It is stated that relatively large proportions of impurities in the glyoxal are prevented by the above procedure.

German Laid-Open Application DOS No. 2,634,439 describes the use of a catalyst which consists of phosphorus in combination with Cu and/or Ag. A bromine compound is added to the reaction mixture, in an amount sufficient to increase the yield of glyoxal but not sufficient markedly to increase the amount of glycol aldehyde formed or to lower the conversion of the ethylene glycol to less than about 90 percent. Inert gas is added. The space-time yield is only 1.5 grams of glyoxal per $cm^3$ of catalyst per hour. A further disadvantage is that the catalyst can be regenerated only by an involved procedure. With regard to the working up of the reaction gases it is stated merely that the gases are fed through a scrubber and condensed constituents are collected in the form of an aqueous solution.

In Ind. and Eng. Chem., Volume 43 (1951), pages 786–794, it is disclosed that the oxidation gases are fed, after oxidation, via a line to the base of a wash tower (1st scrubber), then upward through the wash tower and, via a line, into a wash column (2nd scrubber). In the 1st scrubber, cold glyoxal solution is introduced vertically from above, through 3 nozzles, in countercurrent to the gases. The 2nd scrubber is packed with Raschig rings, through which the glyoxal solution flows in counter-current to the off-gas from the 1st scrubber. It is pointed out that satisfactory condensation of the glyoxal from the oxidation gases can be achieved only in the 2nd scrubber. However, a further formaldehyde stripping column is required to separate off formaldehyde. On leaving the reaction chamber, the oxidation gases are at from 305° to 325° C. An unpublished investigations which we have carried out have shown, the oxidation gases are at from 300° to 320° C. when they enter the bottom of the 1st scrubber. The resulting 32 percent strength by weight glyoxal solutions contain 12.8 percent of unconverted glycol, 5.9 percent of formaldehyde, 1.6 percent of glycolic acid and 0.32 percent of formic acid.

All these processes are unsatisfactory in respect of simple and economical operation coupled with a good yield and high purity of the product, and with regard to the removal of by-products. A further disadvantage is that the cooling units frequently become blocked within an extremely short time, so that continuous operation is considerably impaired. The cracker products and polymers, some of which dissolve in the reaction products obtained, discolor the glyoxal solutions to such an extent that these do not meet the demands made in further processing, especially in the leather, paper and textile industries.

We have found that glyoxal can advantageously be prepared by oxidizing glycol in the presence of a silver catalyst at elevated temperature, cooling the hot reaction gases and separating off the end product, if all or part of the glyoxal, glycol and/or glycol aldehyde, together with water and, if desired, formaldehyde are condensed out of the stream of the reaction mixture, which is in vapor form and at from 450° to 800° C., after the oxidation and not more than one second after the gases have issued from the catalyst, by means of water or aqueous glyoxal solution at from 0° to 130° C. and in the form of droplets having a mean diameter of from 1 to 2,000 micrometers, the majority of the droplets impinging on the stream of reaction gases at an angle of from 2° to 85° to the axis of the stream.

The reaction can be represented by the following equation:

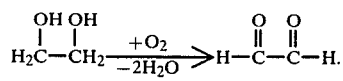

Compared with the conventional processes, the process according to the invention surprisingly gives, more simply and more economically, a better overall result in respect of yield, space-time yield and purity of the end product, and of removal of the by-products. Depending on the choice of conditions according to the invention, aqueous glyoxal solutions of up to 65 percent by weight, preferably of from 30 to 50 percent by weight and in particular of from 38 to 42 percent by weight are obtained. Further advantages of the process according to the invention are the easier removal of the by-products formed during the reaction, in particular of formaldehyde, together with an improvement in the color number of the glyoxal solutions prepared in this way. It is possible by simple means to lower the content of by-products in the resulting glyoxal solution or to remove the total amount of one by-product, for example formaldehyde. The color number of the glyoxal solutions meets even the high demands made in respect of the use of the solutions in the textile, paper and leather industries, without a separate purification stage, for example using ion exchangers, being required. Compared with conventional processes, decomposition of the hot reaction gases and blockages of the pipe connections and installations during cooling are avoided or substantially reduced. In addition, the process makes it possible to remove the formaldehyde from the gas phase by a simple method, so that an involved procedure for purification of the glyoxal solutions becomes unnecessary. Compared with the procedure described in the article in Ind. and Chem. Eng., the process according to the invention gives, using only a single condensation column, a 40 percent strength by weight glyoxal solution containing substantially less formaldehyde, glycol, glycolic acid and formic acid. All these advantageous results are surprising in view of the prior art. In particular, it was not to be expected that the color number of the glyoxal solutions prepared, which is a measure of the impurities, the decomposition of the hot gases during cooling and the formation of cracker products, could be considerably lowered merely by the cooling conditions according to the invention. On the contrary, it is stated in Ind. and Chem. Eng. (loc. cit.) that glyoxal tends, near its dew point, to form horny polymers with small amounts of water. It was also surprising that the end product could be obtained in good yield and high purity by the process according to the invention, even though substantially hotter reaction gases have to be cooled within a very short time. It was also not to be expected that glyoxal could be completely condensed out, from the reaction gases, at temperatures which are distinctly higher than those mentioned in Example 6 of the article in Ind. and Chem. Eng. (loc. cit.). It is stated specifically in this Example that when the gases are cooled to 50° C. it is in the main unconverted ethylene glycol which condenses and some of this forms, with glyoxal, the by-product 2,3-dihydroxydioxane. Glyoxal, water and formaldehyde can only condense on further cooling of the gases to 15° C. When employing the process according to the invention, the undesired formation of the by-product 2,3-dihydroxydioxane is surprisingly not observed.

Suitable starting materials for the process are pure ethylene glycol, technical-grade ethylene glycol or crude ethylene glycol, or advantageously mixtures thereof with water; aqueous mixtures advantageously contain from 30 to 70 percent by weight, preferably from 45 to 55 percent by weight, of ethylene glycol. Advantageously, 49.5–50.5 percent strength by weight solutions, or mixtures of the two components in the same proportions by weight, are used. The ethylene glycol is fed into the reaction chamber in vapor form, advantageously mixed with steam and with or without an inert gas. Advantageously, an inert gas is also used. Examples of suitable gases which are inert under the reaction conditions are advantageously rare gases, eg. xenon, argon, neon or helium; alkanes, eg. methane, ethane, propane, 2,2-dimethylpropane, butane, pentane or isobutane; gaseous organic compounds of inorganic elements, eg. tetramethylsilane; ethers, eg. dimethyl ether or methyl ethyl ether; and preferably nitrogen, carbon monoxide and/or carbon dioxide; and corresponding mixtures. The inert gas can be used on its own or as a mixture with steam and/or glycol vapor or, advantageously, as a mixture with air. The molar ratio of inert gas to oxygen is as a rule not less than from 4.4:1, preferably from 4.4:1 to 20:1 and advantageously from 6:1 to 10:1. The details given with regard to the inert gas always relate to the total amount, ie. including the amount of inert gas in the air, which is preferably used. The off-gas from the reaction may itself also be used as the inert gas since, as a rule, in addition to the inert gases nitrogen, carbon monoxide, carbon dioxide, hydrogen and water vapor, it only contains residues of unconverted starting material, which is thus further utilized.

The oxidizing agent used may be either pure oxygen or gases containing free oxygen, especially air. Oxygen, as a rule in the form of air, and ethylene glycol are advantageously employed in a molar ratio of from 0.5 to 1.2, in particular from 0.7 to 1, moles of oxygen per mole of ethylene glycol. Preferably, the total amount of water vapor is not more than 5 and advantageously from 1 to 4 moles, per mole of ethylene glycol. The air and, where appropriate, the inert gas can be introduced directly into the vaporization stage of the ethylene glycol, advantageously into the boiling ethylene glycol/water mixture, or at any desired point upstream of the catalyst. The residence time in the reaction chamber is appropriately not more than 0.1, advantageously from 0.0005 to 0.05, preferably from 0.001 to 0.03 and preferentially from 0.001 to 0.021 second.

The total thickness of the catalyst bed is advantageously from 15 to 50, preferably from 20 to 30, millimeters. The reaction can be carried out by one of the conventional processes using a silver catalyst, which can be selected as desired from a wide range. Advantageously, however, the reaction is carried out in the presence of silver crystals having a particle size of from 0.1 to 2.5 millimeters. The catalyst particles, in the form of silver crystals, are advantageously present as one layer in a conventionally vertical reactor, or are arranged, according to particle size in an upper and lower layer of the total bed or in an upper, middle and lower layer of the total bed. The entire catalyst bed is advantageously supported on a silver or stainless steel gauze which has been heat-treated. In large reactors, having a diameter of more than 15 cm, the gauze is advantageously corrugated before being fitted into the reactor. It is advantageous to support the gauze on a perforated plate, and to locate the condensation unit according to the invention immediately below the plate. The starting mixture, of ethylene glycol vapor and oxygen or air, with or without water vapor and inert gas, is in general passed downward through the reactor, so that the upper layer or upper layers are the part which faces the starting mixture. In reactors of a different construction, or where the starting mixture is passed through the reaction in a different manner, the remarks in the description relating to the upper (lower) layer of the catalyst correspond to the layer facing the starting mixture (facing the discharged mixture), for example, in the case of a horizontal reactor, the front (rear) layer of the catalyst. If the catalyst has only one layer, this advantageously contains silver crystals having a particle size of from 0.1 to 2.5, advantageously from 0.1 to 2 and preferably from 0.2 to 1 millimeter. In a 2-layer catalyst, the upper layer advantageously comprises from 20 to 60, preferably from 25 to 50, percent by weight of the catalyst, the particle sizes being from 0.1 to 0.75 millimeter, whilst the lower layer comprises from 40 to 80, preferably from 50 to 75, percent by weight of the catalyst, the particle sizes being from 0.75 to 2.5, advantageously from 0.75 to 1, millimeter.

In a 3-layer catalyst, the lower layer advantageously comprises from 72.5 to 89, preferably from 77.5 to 82.5, percent by weight of all catalyst particles, the middle layer comprises from 2.5 to 7.5, preferably from 4.5 to 6.5, percent by weight of all catalyst particles and the upper layer comprises from 8.5 to 20, preferably from 13 to 16, percent by weight of all catalyst particles. The particles in the lower layer advantageously have sizes of from 1 to 2.5 millimeters, those in the middle layer from 0.75 to 1 millimeter and those in the upper layer from 0.1 to 0.75 millimeter.

Advantageously, the throughput used is from 0.2 to 3 t, especially from 0.3 to 1 t, of ethylene glycol per m$^2$ of catalyst bed cross-section per hour. In industrial operation, catalyst bed diameters of at least 0.2 meter, advantageously from 0.5 to 2 meters, are preferred.

For the oxidation, a gaseous mixture consisting of ethylene glycol vapor, air, inert gas and advantageously water vapor is passed, in the above amounts, through the silver catalyst at from 450° to 710° C., preferably from 550° to 660° C. The process is in general carried out continuously under a pressure of from 0.8 to 2 bar, preferably from 0.8 to 1.8 bar and especially from 1.05 to 1.5 bar.

Inhibitors may also be added to the starting mixture, advantageously to the vapor/gas stream of the other components upstream of the catalyst. Examples of advantageous inhibitors are halohydrocarbons, in particular bromo- and chloro-hydrocarbons, eg. tetrachloroethylene, 1,1,2,2- and 1,1,1,2-tetrachloroethane, amyl chloride, cyclohexyl chloride, 1,2-dichloropropane, methylene chloride, dichlorobutane, isopropyl bromide, n-propyl bromide, butyl bromide, chloroform, bromoform, ethyl iodide, propyl iodide, chloronaphthalene, dichloronaphthalene, carbon tetrachloride, 1,1,1- and 1,1,2-trichloroethane, trichloroethylene, pentachloroethane, 1,2-dichloroethane, 1,1-dichloroethane, n-propyl chloride, 1,2-cis-dichloroethylene, n-butyl chloride, 2-, 3-, and iso-butyl chloride, chlorobenzene, fluorobenzene, bromobenzene, iodobenzene, o-, p- and m-dichlorobenzene, o-, p- and m-dibromobenzene, o-, m- and p-chlorotoluene, 1,2,4-trichlorobenzene, 1,10-dibromodecane and 1,4-dibromobutane and mixtures of these compounds. HCl, Cl$_2$ and bromoform are particularly preferred inhibitors. Advantageously, the inhibitor is used in an amount of from 0.01 to 0.8 percent by weight and preferably of from 0.05 to 0.5 percent by weight, based on ethylene glycol.

In the text which follows, the treatment of the hot reaction gases with a liquid in a state of fine dispersion, for the purposes of cooling the gases and completely or partially condensing condensable constituents, is defined as quenching and the operation itself is defined as the quench. The reaction mixture in the vapor/gaseous form (reaction gases) which issues from the catalyst or from the bottom of the final layer of catalyst advantageously contains from 40 to 85 percent by weight of nitrogen, from 0.01 to 1 percent by weight of oxygen, from 0.5 to 4 percent by weight of carbon monoxide, from 1 to 12 percent by weight of carbon dioxide, from 3 to 20 percent by weight of glyoxal, from 0.01 to 1 percent by weight of unconverted ethylene glycol, from 0.01 to 4 percent by weight of glycol aldehyde, from 0.1 to 6 percent by weight of formaldehyde, from 10 to 40 percent by weight of water, from 0.01 to 1 percent by weight of glycolic acid, from 0.01 to 1 percent by weight of glyoxylic acid, from 0.01 to 1 percent by weight of formic acid, from 0.001 to 0.1 percent by weight of 2-hydroxymethyldioxolane and from 0.1 to 2 percent by weight of hydrogen.

The flow rate of the reaction gases is advantageously from 0.1 to 10, in particular from 0.1 to 5, meters per second. The residence time of the reaction gases between the catalyst chamber and the quenching chamber is not more than one second, appropriately not more than 0.1 second, advantageously from 0.001 to 0.05 second and in particular from 0.001 to 0.01 second. The residence time in the quenching chamber is not more than one second, advantageously from 0.01 to 0.5 second and in particular from 0.04 to 0.2 second. The quenching chamber is defined as the zone in which the treatment with the quenching liquid is carried out.

The quench is carried out with the quenching liquid, ie. water or, preferably, aqueous glyoxal solution, in which other substances may also be present, these advantageously being starting materials or byproducts from the glyoxal synthesis, for example ethylene glycol, glycol aldehyde, glycolic acid, glyoxylic acid, formaldehyde, formic acid and 2-hydroxymethyldioxolane. The glyoxal solutions used are advantageously those obtained from the preparation of glyoxal, and containing from 0.01 to 5, in particular from 0.01 to 3, percent by weight of ethylene glycol, from 0.1 to 20, in particular from 0.1 to 10, percent by weight of glycol aldehyde, from 0.01 to 5, in particular from 0.01 to 3, percent by weight of glycolic acid, from 0.01 to 5, in particular from 0.01 to 3, percent by weight of glyoxylic acid, from 0.1 to 10, in particular from 0.05 to 5, percent by weight of formaldehyde, from 0.01 to 5, in particular from 0.01 to 3, percent by weight of formic acid and from 0.05 to 0.5, in particular from 0.05 to 0.2, percent by weight of 2-hydroxymethyldioxolane. The quenching liquid, which is advantageously at 10°–120° C. and in particular at 30°–110° C., is fed, after cooling or heating if necessary, to a disperser. Dispersers which can be used are advantageously those possessing mixers, atomizers and, preferably, nozzles as the dispersing device, eg. injector mixers, mixing chambers or mixing zones possessing injectors, jet mixers, equipment possessing vortex nozzles, eccentric nozzles, bundle nozzles, centrifugal pressure nozzles, slit nozzles, fan nozzles, hollow nozzles, spiral nozzles and in particular atomizer nozzles, two-material mixing nozzles, rotating atomizers, impact jets, solid cone jets, rotating atomizer discs with vanes, rotating atomizer discs with nozzles, slip nozzles, Siccatom nozzles and hollow cone nozzles. The dispersing apparatus used can comprise one or preferably several, advantageously from 4 to 20, of the above nozzles per meter of the mean diameter of the quenching chamber. The quenching liquid which passes into the inlet part of the disperser, eg. the nozzle chamber is dispersed in the dispersing section, eg. in the nozzle, to form droplets having a mean diameter of from 1 to 2,000, preferably of from 1 to 200, micrometers. The droplets formed impinge on the reaction gases downstream of the outlet part of the disperser, eg. downstream of the nozzle.

Advantageously, the dispersing devices, which as a rule are nozzles, are located directly behind or below the outlet from the catalyst chamber (reaction chamber) or from the final layer of the catalyst, advantageously at or, in particular, behind or below the reactor outlet. Preferably, the nozzles are located at the top of a wash tower or, advantageously, of a quenching column, eg. a packed or tray column, and the reactor outlet is advantageously located above the wash tower or the quenching column, so that the reaction gases, after issuing from the reaction chamber, pass immediately into the quenching chamber. The nozzles can be arranged in the quenching chamber as desired, eg. as a bundle in the center of the quenching chamber cross-section (column cross-section), or distributed at equal distances from one another or from the wall. Advantageously, they are distributed in the form of a ring at or near the wall of the quenching chamber (or the column), each nozzle being at the same distance from the two adjacent nozzles. In a preferred arrangement, from 2 to 5, advantageously from 2 to 3, such rings are formed one behind the other, each ring being at or near the column wall and advantageously possessing from 4 to 20 and in particular from 8 to 16 nozzles per meter of the mean diameter of the quenching chamber. Advantageously, the nozzles in each ring are arranged so that they coincide with spaces in the preceding and/or following ring. Advantageously, a tubular quenching chamber (column) is employed which has a length/diameter ratio of from 0.1 to 3, in particular from 0.2 to 1. In general, the rings of nozzles are spaced apart in such a way that the entire quenching chamber, including the space above the wall of the quenching chamber (column wall), is uniformly filled with the gas/vapor/liquid mist of the finely dispersed mixture of droplets and constituents in the gaseous or vapor form.

As a rule, the nozzles are so arranged that the liquid which issues therefrom sweeps over the entire chamber, or rebounds from the walls of the quenching chamber; in this way the quenching chamber constitutes a layer of liquid/gas mist onto which the hot reaction gases impinge. The outlet from a nozzle is not parallel to the axis of flow of the reaction gases; instead, all nozzle outlets or axes are at an angle to the axis of flow, so that most of the droplets sprayed by the jet, ie. advantageously from 60 to 100, in particular from 60 to 80, percent by weight of the entire quenching liquid, impinge on the stream of reaction gases at an angle which is advantageously of from 15 to 85, appropriately from 20 to 85, preferably from 25 to 82 and in particular from 30° to 80° to the axis of flow. By arranging the nozzles in a ring, as stated above to be preferred, the rings being at or near the wall at the top of the quenching column, and by positioning the jets at preferably different angles, the liquid/gas mist is advantageously uniformly distributed within the quenching chamber and over the column wall. When measuring the angle, 0 is defined as parallel to the axis of flow and 90 as vertical thereto. Preferably, the angles are set so that the nozzles spray the quenching liquid at the above angle to the axis of flow and in countercurrent to the reaction gases; however, it is also possible to spray the quenching liquid in co-current, ie. the outlets of the nozzles are arranged in the direction of flow at the above angles to the axis of flow. Advantageously, from 0.5 to 60, preferably from 1 to 40, kilograms of water or aqueous glyoxal solution are used per kilogram of reaction gases. The amount of inert gas is advantageously from 50 to 95, in particular from 70 to 95, percent by weight, based on the total weight of the reaction gases, the residence time of the reaction gases in the quenching chamber is from 0.01 to 0.5, in particular from 0.04 to 0.2, second and that part of the reaction gas which issues from the quenching chamber (ie. the off-gas) is at up to 150° C., in particular at 25°–120° C., and has a flow rate of from 0.1 to 10, in particular from 0.1 to 5, meters per second. During the quench, which is carried out continuously, water is always condensed and glyoxal, glycol and/or glycol aldehyde may be condensed, depending on the particular conditions. All or part of the formaldehyde, glycolic acid, glyoxylic acid, formic acid and/or 2-hydroxymethyldioxolane contained in the reaction gases is obtained in the condensate from the quench, as desired.

By suitably selecting the above parameters, in particular the nature of the quenching liquid and its temperature and amount, the amount of inert gas in the stream of reaction gas and the residence time of the gases in the quenching chamber, all or some of the condensable constituents can be condensed in the quenching chamber. The higher (a) the temperature of the quenching liquid, which is advantageously at from 10° to 120° C., the lower (b) the amount of quenching liquid, which is advantageously from 0.5 to 60 kilograms of water or aqueous glyoxal solution per kilogram of reaction gases, and the larger (c) the amount of inert gas, which advantageously is from 50 to 95 percent by weight, based on the weight of the reaction gases, the smaller is the amount of condensate. If, within the above advantageous ranges, (a) the temperature of the quenching liquid is lowered from 120° to 0° C., from 40 to 100 percent by weight of the total amount of glycol aldehyde in the reaction gases can be condensed, corresponding (in each case based on the total amount of the particular substance in the reaction gases) to from 80 to 100 percent by weight of glycol, from 5 to 100 percent by weight of glyoxal, from 0 to 100 percent by weight of formaldehyde and from 4 to 100 percent by weight of water, the amounts condensed rising correspondingly as the temperature falls. If, in accordance with the above advantageous ranges, (b) is increased from 0.5 to 60 kilograms of water per kilogram of reaction gases, a condensate containing (in each case based on the total amount of the particular substance in the reaction gases) from 75 to 100 percent by weight of glycol aldehyde, from 80 to 100 percent by weight of glycol, from 5 to 100 percent by weight of glyoxal, from 0.5 to 97 percent by weight of formaldehyde and from 4 to 95 percent by weight of water is obtained, the amounts condensed increasing correspondingly as (b) is increased. If, within the above advantageous ranges, (c) the amount of inert gas is reduced from 95 to 50 percent by weight, based on the weight of the reaction gases, a condensate containing (in each case based on the total amount of the particular substance in the reaction gases) from 80 to 100 percent by weight of glycol aldehyde, from 85 to 100 percent by weight of glycol, from 5 to 100 percent by weight of glyoxal, from 0 to 97 percent by weight of formaldehyde and from 4 to 95 percent by weight of water is obtained, the amounts condensed increasing correspondingly as (c) is reduced. If, (d) the residence time of the reaction gases in the quenching chamber is extended, eg. from 0.01 to 0.7 second, it is possible to condense (in each case based on the total amount of the particular substance in the reaction gases) from 50 to 100 percent by weight of glycol aldehyde, from 70 to 100 percent by weight of glycol, from 0 to 100 percent by weight of glyoxal, from 0 to 97 percent by weight of formaldehyde and from 4 to 95 percent by weight of water, the amounts condensed increasing correspondingly as (d) is extended. If the concentration of the aqueous glyoxal solution is increased from above 0 (water) to 65 percent by weight, there is a corresponding increase in the concentration, in the condensate, of glyoxal from 0 to 65 percent by weight, of glycol from 0.01 to 5 percent by weight, of formaldehyde from 0.1 to 10 percent by weight and of glycol aldehyde from 0.1 to 20 percent by weight. By way of example, the constituents listed in the Table which follows are obtained in the condensate in the proportions indicated, based on the total amount of the particular substance in the reaction gases, under the indicated conditions. A specific ratio of the constituents in the condensate from the quenching column can thus be established easily by means of a few experiments.

TABLE

| Proportions in % by weight in the condensate | Temperature of the quenching liquid in °C. | Glyoxal content, in % by weight, in the quenching liquid | Amount of quenching liquid in kg per kg of reaction gas | Residence time of the reaction gases in the quenching chamber, in seconds | Amount of inert gas in % by weight, based on the reaction gases |
|---|---|---|---|---|---|
| Glyoxal 50; glycol 90; glycol aldehyde 90; water 10; $CH_2O$ 2 | 92 | 21 | 20 | 0.08 | 85 |
| Glyoxal 20; glycol 90; glycol aldehyde 80; water 5; $CH_2O$ 1 | 95 | 11 | 6 | 0.05 | 90 |
| Glyoxal 100; glycol 100; glycol aldehyde 100; water 80; $CH_2O$ 95 | 25 | 24 | 33 | 0.12 | 70 |
| Glyoxal 80; glycol 100; glycol aldehyde 95; water 15; $CH_2O$ 10 | 90 | 42 | 23 | 0.1 | 86 |
| Glyoxal 100; glycol 100; glycol aldehyde 100; water 50; $CH_2O$ 60 | 70 | 50 | 50 | 0.09 | 92 |
| Glyoxal 90; glycol 100; glycol aldehyde 98; water 30; $CH_2O$ 12 | 88 | 40 | 30 | 0.1 | 85 |
| Glyoxal 100; Glycol 100; glycol aldehyde 100; water 95; $CH_2O$ 97 | 10 | 23 | 60 | 0.2 | 50 |
| Glyoxal 70; glycol 95; | 95 | 36 | 15 | 0.09 | 84 |

TABLE-continued

| Proportions in % by weight in the condensate | Temperature of the quenching liquid in °C. | Glyoxal content, in % by weight, in the quenching liquid | Amount of quenching liquid in kg per kg of reaction gas | Residence time of the reaction gases in the quenching chamber, in seconds | Amount of inert gas in % by weight, based on the reaction gases |
|---|---|---|---|---|---|
| glycol aldehyde 92; water 10; CH$_2$O 3 | | | | | |

As a rule, under the above conditions, glycolic acid behaves similarly to glycol, glyoxylic acid similarly to glycol, formic acid similarly to water and 2-hydroxymethyldioxolane similarly to glycol aldehyde in respect of the condensation characteristics and the above constituents can be wholly or partially condensed under the conditions given above for the comparable substances.

Under the above conditions according to the invention, the resulting 0-65 percent strength by weight glyoxal solutions contain in general from 0.01 to 5, in particular from 0.01 to 3, percent by weight of glycol, from 0.1 to 20, in particular from 0.1 to 10, percent by weight of glycol aldehyde, from 0.1 to 10, in particular from 0.1 to 5, percent by weight of formaldehyde, from 0.01 to 5, in particular from 0.01 to 3, percent by weight of glycolic acid, from 0.01 to 5, in particular from 0.01 to 3, percent by weight of glyoxylic acid, from 0.01 to 5, in particular from 0.01 to 3, percent by weight of formic acid and from 0.05 to 0.5, in particular from 0.05 to 0.2, percent by weight of 2-hydroxymethyldioxolane. The quenching liquid can be taken direct from the above glyoxal solution and, if desired, diluted with water; glyoxal solutions obtained from another production installation may also be used as the quenching liquid, but advantageously have the above composition.

In an advantageous embodiment of the process, all, or as a rule some, of the off-gas which remains after separating off the condensate is fed back into the reaction. Accordingly, the condensation conditions can also be so adjusted that all the formaldehyde remains in the off-gas and is removed or is separated off as an aqueous 5-60 percent strength by weight solution in a further absorption column. All of the condensate can be withdrawn as ready-for-use glyoxal solution, or a part thereof can be circulated as coolant. It is thus possible, by the process according to the invention, to prepare, in a multi-stage condensation, a virtually formaldehyde-free solution and, at the same time, a solution enriched with formaldehyde. By suitably selecting the values of the above parameters, for example, only some of the glyoxal is condensed out in the first column, the remaining glyoxal being collected, together with the formaldehyde, in aqueous solution in a second column. Since, on the one hand, formaldehyde-free glyoxal solution and, on the other hand, glyoxal solution enriched with formaldehyde are frequently required for industrial purposes, it is an advantage of the process according to the invention that these different demands in respect of quality can be met in a single installation. In general, depending on the choice of the above conditions, it is possible to condense and separate off, in the quenching chamber and thus also in the first column, from 0 to 100 percent by weight of glyoxal, from 70 to 100 percent by weight of glycol, from 50 to 100 percent by weight of glycol aldehyde, from 4 to 100 percent by weight of water, from 0 to 100 percent by weight of formic acid, from 50 to 100 percent by weight of 2-hydroxymethyldioxolane and from 70 to 100 percent by weight of glyoxylic acid, based on the amount of the particular substance originally present in the reaction gases.

In general, the aqueous solutions, advantageously of 40 percent strength by weight, are used further direct; the product may or may not be isolated in a conventional manner, eg. by distillation with dehydrating agents.

The glyoxal which can be prepared by the process of the invention is a wrinkle-resist agent, an assistant for increasing the tear strength and elasticity of fiber materials, a tanning agent, a photographic hardener and a valuable starting material for the preparation of synthetic resins, textile assistants, eg. for preventing shrinkage after washing, paper assistants, eg. for increasing the wet strength, and plastics. With regard to the use of glyoxal, reference should be made to the publications mentioned above and to Ullmann (loc. cit.)

In the Examples which follow, parts are by weight.

EXAMPLE 1

(The figures in brackets relate to FIG. 1)

(a) The apparatus used comprises an ethylene glycol vaporizer (1), feed lines for ethylene glycol (6), water (7) and air or nitrogen (11) and a vertical tubular reactor (2). At its top, the reactor is equipped with a feed line (12) for the vaporous starting mixture, and with the reactor cover. The catalyst bed is located below the reactor top, and below the catalyst bed is the quenching chamber (10), which forms the top of a packed column (3). Some of the condensate is used as quenching liquid which is sprayed, by means of a pump (4) and via a heat exchanger (5) and a nozzle system, directly behind the catalyst bed into the hot gases, which are cooled to 7° C. and partially condensed in the quenching chamber, a 27.5 percent strength by weight glyoxal solution being withdrawn via line (8). The off-gas escapes via line (9).

A catalyst comprising 45 parts of silver crystals and having the following composition is introduced into the reactor (2):

|  | Amount of catalyst (% by weight) | Particle size mm |
|---|---|---|
| Layer 1 | 15 | 0.1-0.75 |
| Layer 2 | 5 | 0.75-1 |
| Layer 3 | 80 | 1-2.5 |

The height of the bed is 30 mm. Per hour, a mixture of 246 parts of ethylene glycol, 246 parts of water, 456 parts of air and 340 parts of nitrogen is fed to the vaporizer (1) and vaporized therein. The vaporous starting mixture is passed through the catalyst and is reacted at 597° C. and 1.12 bar. The residence time in the catalyst chamber is 0.01 second. The reaction gases (1,288 parts per hour) which pass into the quenching chamber contain 53.7 percent by weight of $N_2$, 0.2 percent by weight of $O_2$, 1.6 percent by weight of CO, 3.4 percent by weight of $CO_2$, 10.7 percent by weight of glyoxal, 0.4 percent by weight of ethylene glycol, 26.5 percent by weight of water, 0.7 percent by weight of formaldehyde, 2 percent by weight of glycol aldehyde, 0.05 percent by weight of glycolic acid, 0.1 percent by weight of formic acid, 0.005 percent by weight of 2-hydroxymethyldioxolane, 0.04 percent by weight of glyoxylic acid and 0.3 percent by weight of hydrogen.

The reaction gases have a flow rate of 2.6 meters per second and a residence time between the catalyst bed and the quenching chamber of 0.004 second; the gases, which are at 580° C. before entering the quenching chamber, have a residence time therein of 0.11 second and issue therefrom at 85° C., the amount of quenching liquid, which is at 70° C., being 8,000 parts per hour.

2 rings of nozzles are used; each ring comprises 6 nozzles arranged so that the nozzles in one ring coincide with the gaps in the other. The nozzles of a ring are located at the column wall and are arranged symmetrically. The angle at which the droplets impinge relative to the axis of flow is different for all the nozzles and is from 15° to 75°, 70% of the droplets impinging at an angle of from 30° to 75°. The droplets have a mean diameter of 200 micrometers. 337 parts of 41 percent strength by weight glyoxal solution, or 138 parts per hour of glyoxal, are obtained, corresponding to a yield of 60% of theory, based on glycol used. The catalyst life is 90 days. The glyoxal solution (and thus the quenching liquid) contains 1.6 percent by weight of ethylene glycol, 1.4 percent by weight of formaldehyde, 8.2 percent by weight of glycol aldehyde, 0.2 percent by weight of glycolic acid, 0.4 percent by weight of formic acid, 0.07 percent by weight of 2-hydroxymethyldioxolane, and 0.2 percent by weight of glyoxylic acid. The conversion is 97.8 percent and the space-time yield is 14.7 g of glyoxal per $cm^3$ of catalyst per hour. The color number of the solution after three days' operation is 22, the color number being determined by means of the platinum/cobalt scale according to ASTM D 1209-69. No solid residues form even during an operating period of 30 days.

(b) Comparison:

In place of the quenching chamber (10) and the packed column (3), the apparatus has two water-cooled condensation columns connected downstream of the reactor. The reaction is carried out as described in Example 1. The reaction gases are cooled to 200° C. in the first cooling zone and to 10° C. in the 2nd cooling zone, all condensable vapors being obtained in liquid form. 498 parts of 25.3 percent strength by weight glyoxal solution, or 126 parts per hour of glyoxal, are obtained, corresponding to a yield of 55% of theory. The glyoxal solution contains one percent by weight of glycol and 1.8 percent by weight of formaldehyde, 5.2 percent by weight of glycol aldehyde, 0.3 percent of weight of glycolic acid, 0.4 percent by weight of formic acid, 0.07 percent by weight of 2-hydroxymethyldioxolane and 0.3 percent by weight of glyoxylic acid. The conversion is 97.8 percent and the space-time yield is 13.5 grams of glyoxal per $cm^3$ of catalyst per hour. The color number of the solution after three days' operation is 500, the color number being determined by means of the platinum/cobalt scale according to ASTM D 1209-69. After an operating period of 3 days, 12 parts of cracker residues are found in the first condenser.

Figure 2:
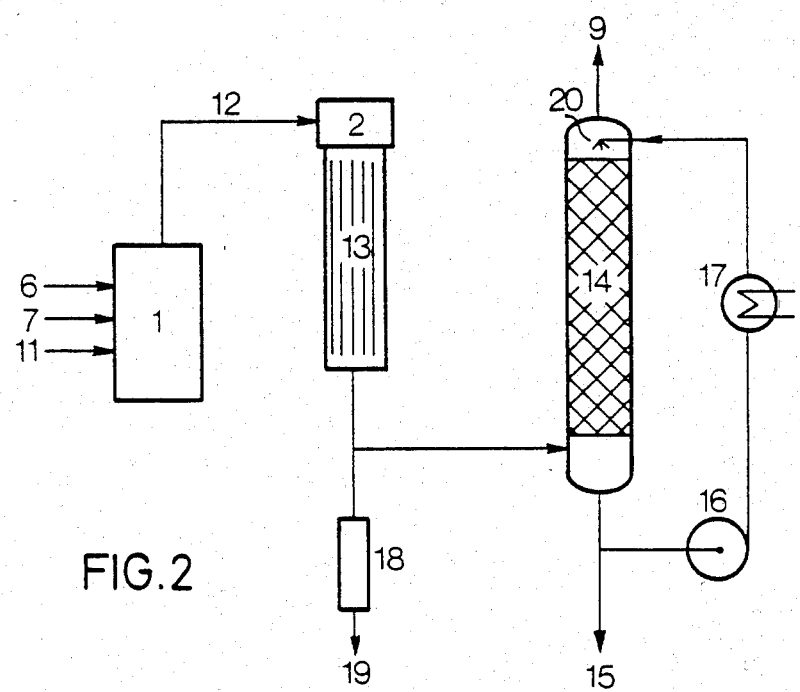
Figure 3:
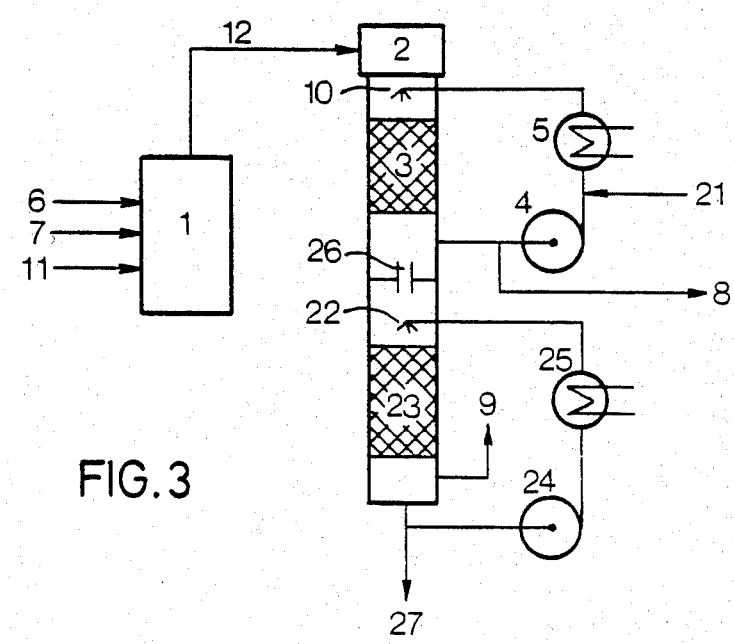

(c) Comparison (FIG. 2):

The reaction is carried out as described in Example 1(a); in place of the quenching chamber, a tubular heat exchanger (13) flange-mounted to a vertical tubular reactor (2) is used and the hot reaction gases are cooled to 190° C. in this heat exchanger. The condensable vapors are washed out in the downstream adsorption column (14). The resulting 21.6 percent strength by weight glyoxal solution is used as the coolant and washing liquid. Part of the solution is withdrawn from the apparatus via line (15) and the remainder is circulated by means of a pump (16) through the heat exchanger (17), in which the washing liquid is cooled to 20° C. 8,000 parts/hour of washing liquid impinge in countercurrent from 6 nozzles (20) frontally onto the reaction gases, the angle to the axis of flow being 0. The residence time between the catalyst and the nozzles is 1.2 seconds and the gases are at 170° C. prior to the wash. Any condensate obtained in the tubular heat exchanger (13) collects in the receiver (18) and is removed from the apparatus via line (19). The off-gas escapes via line (9). The substances fed in via lines (6), (11), (12) and (7) and the arrangement of the catalyst layers in the reactor (2) are chosen to be similar to those in Example 1.

508 parts of 21.6 percent strength by weight glyoxal solution, or 110 parts per hour of glyoxal, are obtained, corresponding to a yield of 48% of theory. The glyoxal solution contains one percent by weight of glycol and 3.5 percent by weight of formaldehyde, 5.1 percent by weight of glycol aldehyde, 0.5 percent by weight of glycolic acid, 0.7 percent by weight of formic acid, 0.07 percent by weight of 2-hydroxymethyldioxolane and 0.6 percent by weight of glyoxylic acid. The color number of the solution after an operating period of 10 days is 800, the color number being determined by means of the platinum/cobalt scale according to ASTM D 1209-69. After the above operation period, the tubes of the heat exchanger (13) downstream of the reactor are blocked by deposits of cracker products.

EXAMPLE 2

The reaction is carried out by a method similar to that described in Example 1, the same apparatus being used and only the quenching conditions being changed. 2 rings of nozzles are used; each ring comprises 6 nozzles arranged so that the nozzles in one ring coincide with the gaps in the other. The nozzles of a ring are located at the column wall and are arranged symmetrically. The angle at which the droplets impinge relative to the axis of flow is different for all the nozzles and is from 15° to 75°, 70% of the droplets impinging at an angle of from 30° to 75°. The droplets have a mean diameter of 200 micrometers. The reaction gases have a flow rate of 2.6 meters per second and a residence time between the catalyst bed and the quenching chamber of 0.004 second; the gases, which are at 580° C. before entering the quenching chamber, have a residence time therein of 0.08 second and issue therefrom at 85° C., the amount of quenching liquid, which is at 65° C., being 7,000 parts per hour.

345 parts of a 40 percent strength by weight glyoxal solution, or 138 parts per hour of glyoxal, are obtained, corresponding to a yield of 60% of theory. The catalyst life is 90 days. The glyoxal solution (and thus the quenching liquid) contains 1.5 percent by weight of glycol, 0.9 percent by weight of formaldehyde, 8.1 percent by weight of glycol aldehyde, 0.2 percent by weight ot glycolic acid, 0.4 percent by weight of formic acid, 0.07 percent by weight of 2-hydroxymethyldioxolane and 0.2 percent by weight of glyoxylic acid. The conversion is 97.8 percent and the spacetime yield is 14.6 grams of glyoxal per cm$^3$ of catalyst per hour. The color number of the solution after an operating period of three days is 15, the color number being determined by means of the platinum/cobalt scale according to ASTM D 1209-69. No solid residues form even during an operating period of 30 days.

EXAMPLE 3

The reaction is carried out in a manner similar to that described in Example 1, the same apparatus being used. The feed of nitrogen via line (11) is increased to 1,400 parts per hour and the air feed is increased to 520 parts per hour. In addition, 250 parts of water per hour are added to the quenching liquid via line (21). The reaction gases (2,412 parts per hour) which pass into the quenching chamber contain 74.6 percent by weight of $N_2$, 0.1 percent by weight of $O_2$, 0.9 percent by weight of CO, 1.9 percent by weight of $CO_2$, 5.9 percent by weight of glyoxal, 0.2 percent by weight of ethylene glycol, 14.3 percent by weight of water, 0.4 percent by weight of formaldehyde, 1.1 percent by weight of glycol aldehyde, 0.04 percent by weight of glycolic acid, 0.05 percent by weight of formic acid, 0.005 percent by weight of 2-hydroxymethyldioxolane, 0.05 percent by weight of glyoxylic acid and 0.1 percent by weight of hydrogen. The reaction gases have a flow rate of 4.7 meters per second and a residence time between the catalyst bed and the quenching chamber of 0.002 second; the gases, which are at 580° C. before entering the quenching chamber, have a residence time therein of 0.06 second and issue therefrom at 65° C., the amount of quenching liquid, which is at 60° C., being 8,000 parts per hour.

358 parts of 40 percent strength by weight glyoxal solution, or 143 parts per hour of glyoxal, are obtained, corresponding to a yield of 62% of theory. The catalyst life is 90 days. The glyoxal solution contains 1.5 percent by weight of glycol, 0.2 percent by weight of formaldehyde, 6.9 percent by weight of glycol aldehyde, 0.2 percent by weight of glycolic acid, 0.4 percent by weight of formic acid, 0.07 percent by weight of 2-hydroxymethyldioxolane and 0.2 percent by weight of glyoxylic acid. The quenching liquid contains 37.7 percent by weight of glyoxal, 1.4 percent by weight of glycol, 0.2 percent by weight of formaldehyde, 6.5 percent by weight of glycol aldehyde, 0.2 percent by weight of glycolic acid, 0.4 percent by weight of formic acid, 0.07 percent by weight of 2-hydroxymethyldioxolane and 0.2 percent by weight of glyoxylic acid. The color number of the solution after an operating period of three days is 14, the color number being determined by means of the platinum/cobalt scale according to ASTM D 1209-69. No solid residues form even during an operating period of 30 days.

EXAMPLE 4 (FIG. 3)

The reaction is carried out by a method similar to that described in Example 1. The apparatus corresponds to that described therein (FIG. 1), except that it comprises, in addition to the quenching chamber (10) and the packed column (3), an additional quenching chamber (22) and a packed column (23), which are located immediately downstream of the first quench. The quenching liquid in the second circulation system is sprayed in a vortex, by means of a pump (24) and via a heat exchanger (25) and a nozzle system, into the gases which enter via line (26). The gases are cooled and condensed in the quenching chamber, and a 40 percent strength by weight glyoxal solution is withdrawn via line (27). Some of the condensate is used as quenching liquid. The off-gas escapes via line (9). The nozzle system, the diameter of the droplets and the angle at which these impinge on the gas are as described in Example 1.

Per hour, an additional 400 parts of water are fed to the quenching liquid via line (21). The reaction gases (2,412 parts per hour) which pass into the quenching chamber contain 74.6 percent by weight of $N_2$, 0.1 percent by weight of $O_2$, 0.9 percent by weight of CO, 1.9 percent by weight of $CO_2$, 5.9 percent by weight of glyoxal, 0.2 percent by weight of ethylene glycol, 14.6 percent by weight of water, 0.4 percent by weight of formaldehyde, 1.1 percent by weight of glycol aldehyde, 0.04 percent by weight of glycolic acid, 0.05 percent by weight of formic acid, 0.005 percent by weight of 2-hydroxymethyldioxolane, 0.05 percent by weight of glyoxylic acid and 0.2 percent by weight of hydrogen. The reaction gases have a flow rate of 4.7 meters per second and a residence time between the catalyst layer and the quenching chamber of 0.002 second; the gases, which are at 580° C. before entering the quenching chamber (10), have a residence time therein of 0.05 second and issue from the packed column (3) at 85° C., and the amount of quenching liquid, which is at 75° C., in the first cooling circulation system is 5,000 parts per hour.

298 parts of 40 percent strength by weight glyoxal solution, or 119 parts per hour of glyoxal, are withdrawn via line (8); this corresponds to a first partial yield of 51.7% of theory. The glyoxal solution contains 1.8 percent by weight of glycol and 0.1 percent by weight of formaldehyde, 7.8 percent by weight of glycol aldehyde, 0.2 percent by weight of glycolic acid, 0.1 percent by weight of formic acid, 0.06 percent by weight of 2-hydroxymethyldioxolane and 0.2 percent by weight of glyoxylic acid. The quenching liquid contains 34.5 percent by weight of glyoxal, 1.6 percent by weight of glycol, 0.08 percent by weight of formaldehyde, 6.7 percent by weight of glycol aldehyde, 0.2 percent by weight of glycolic acid, 0.05 percent by weight of formic acid, 0.005 percent by weight of 2-hydroxymethyldioxolane and 0.2 percent by weight of glyoxylic acid. The color number of the solution after an operating period of three days is 22, the color number being determined by means of the platinum/cobalt scale according to ASTM D 1209-69. No solid residues form even during an operating period of 30 days. The reaction gases, which are at 85° C. before entering the second quenching chamber (22), have a residence time therein of 0.05 second and issue therefrom at 78° C. and the amount of quenching liquid, which is at 73° C., in the second cooling circulation system is 1,000 parts per hour.

60 parts of 40 percent strength by weight glyoxal solution, or 24 parts per hour of glyoxal, are withdrawn via line (27); this corresponds to a second partial yield of 10.3% of theory. The glyoxal solution contains 0.05 percent by weight of glycol, 14.8 percent by weight of formaldehyde, 5 percent by weight of glycol aldehyde, 0.05 percent by weight of glycolic acid, 3.5 percent by weight of formic acid and 0.05 percent by weight of glyoxylic acid. The color number of the solution after an operating period of three days is 12, the color number being determined by means of the platinum/cobalt scale according to ASTM D 1209-69. No solid residues form even during an operating period of 30 days.

We claim:

1. A process for the continuous preparation of glyoxal by oxidizing glycol with an oxidizing agent in the presence of a silver catalyst at elevated temperature, cooling the hot reaction gases and separating off the end product, wherein all or part of the glyoxal, glycol and/or glycol aldehyde, together with water are condensed out of the hot stream of the reaction mixture, which is in vapor form and at from 450° to 800° C., after the oxidation and not more than one second after the gases have issued from the catalyst, by means of water or aqueous glyoxal solution at from 0° to 130° C. and in the form of droplets having a mean diameter of from 1 to 2,000 micrometers, the majority of the droplets impinging on the stream of reaction gases at an angle of from 2° to 85° to the axis of the stream.

2. The process of claim 1, wherein the glycol oxidation takes place in the presence of an inert gas and wherein the inert gas is used in a molar ratio of inert gas to oxygen of at least 4.4 to 1.

3. The process of claim 1, wherein the glycol is ethylene glycol and wherein a molar ratio of from 0.5 to 1.2 moles of oxygen per mole of ethylene glycol is used.

4. The process of claim 1 or 3, wherein the glycol is ethylene glycol and wherein water vapor is used in an amount of not more than 5 moles per mole of ethylene glycol.

5. The process of claim 1, wherein a gas mixture of ethylene glycol vapor, air, inert gas and water vapor, at from 450° to 710° C. and under a pressure of from 0.8 to 2 bar, is used for the oxidation.

6. The process of claim 1 or 5, wherein an inhibitor is used in an amount of from 0.01 to 0.8 percent by weight, based on ethylene glycol.

7. The process of claim 1, wherein the flow rate of the reaction gases is from 0.1 to 10 meters per second.

8. The process of claim 1, wherein the residence time of the reaction gases between the catalyst chamber and the quenching chamber is not more than one second.

9. The process of claim 1, wherein the residence time in the quenching chamber is not more than one second.

10. The process of claim 1, wherein glyoxal solutions containing from 0.01 to 5 percent by weight of ethylene glycol, from 0.1 to 20 percent by weight of glycol aldehyde, from 0.01 to 5 percent by weight of glycolic acid, from 0.01 to 5 percent by weight of glyoxylic acid, from 0.1 to 10 percent by weight of formaldehyde, from 0.01 to 5 percent by weight of formic acid and from 0.05 to 0.5 percent by weight of 2-hydroxymethyldioxolane are used as the quenching liquid.

11. The process of claim 1, wherein the quenching liquid is at from 10° to 120° C.

12. The process of claim 1, wherein droplets having a mean diameter of from 1 to 200 micrometers are used.

13. The process of claim 1, wherein from 60 to 100 percent by weight of the entire quenching liquid is at an angle of from 15° to 85° to the axis of flow.

14. The process of claim 1, wherein from 0.5 to 60 kilograms of water or aqueous glyoxal solution are used per kilogram of reaction gases.

15. The process of claim 1, wherein the quenching liquid is at from 10° to 120° C., from 0.5 to 60 kilograms of water or aqueous glyoxal solution, per kilogram of reaction gases, are employed as the quenching liquid and the inert gases are used in an amount of from 50 to 95 percent by weight, based on the weight of the reaction gases.

16. The process of claim 1, wherein all or part of the off-gas which remains after separating off the condensate is recycled.

17. The process of claim 1, wherein the hot reaction gases include formaldehyde and wherein all the formaldehyde remains in the off-gas and is separated off as an aqueous 5–60% strength by weight solution in a further absorption column.

* * * * *